United States Patent [19]

von Bebenburg et al.

[11] 4,247,556
[45] Jan. 27, 1981

[54] 7-AZABENZIMIDAZOLES WITH BASIC SIDE CHAINS AND USE THEREOF

[75] Inventors: Walter von Bebenburg, Dreieich; Istvan Szelenyi, Worfelden; Klaus Thiemer, Hanau, all of Fed. Rep. of Germany

[73] Assignee: Deutsche Gold- und Silber-Scheideanstalt vormals Roessler, Frankfurt, Fed. Rep. of Germany

[21] Appl. No.: 3,385

[22] Filed: Jan. 15, 1979

Related U.S. Application Data

[63] Continuation-in-part of Ser. No. 947,528, Oct. 2, 1978, abandoned, and a continuation-in-part of Ser. No. 942,813, Sep. 15, 1978, abandoned.

[30] Foreign Application Priority Data

Sep. 26, 1977 [GB] United Kingdom ............... 39919/77

[51] Int. Cl.³ ..................... A61K 31/44; C07D 471/04
[52] U.S. Cl. ............................. 424/256; 260/244.4; 424/248.52; 424/248.54; 424/248.56; 424/248.57; 424/250; 424/251; 544/63; 544/96; 544/127; 544/238; 544/333; 544/362; 546/118
[58] Field of Search .................... 546/118; 424/256

[56] References Cited

U.S. PATENT DOCUMENTS

| | | | |
|---|---|---|---|
| 2,987,518 | 6/1961 | Hoffmann et al. | 546/118 |
| 3,004,978 | 10/1961 | Hunger et al. | 546/118 |
| 3,719,683 | 3/1973 | Robison et al. | 260/294.8 C |
| 4,059,584 | 11/1977 | Kadin | 546/118 X |
| 4,144,341 | 3/1979 | Clark et al. | 546/118 X |

OTHER PUBLICATIONS

Takadi, Jap. J. Pharmac., vol. 19, (1969), pp. 418–426.
Goldenberg, Gastroenterology, vol. 69, (1975), pp. 636–640.

*Primary Examiner*—Richard Raymond
*Attorney, Agent, or Firm*—Cushman, Darby & Cushman

[57] ABSTRACT

There are prepared 7-azabenzimidazoles of the formula

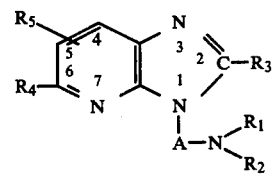

where $R_1$ and $R_2$ are the same or different and are hydrogen, $C_1$–$C_6$-alkyl or $C_2$–$C_6$-alkanol or —$NR_1R_2$ is a 5 to 7 membered saturated heterocyclic ring having either one nitrogen atom, one nitrogen atom and one oxygen atom or two nitrogen atoms, $R_3$ is hydroxy, an amino group, a mono $C_1$–$C_6$-Alkylamino group, a di-$C_1$–$C_6$-alkylamino group, or a $C_2$–$C_6$-alkylamino, di-$C_1$–$C_6$-alkylamino, mercapto, $C_1$–$C_6$-alkylmercapto, hydroxy or $C_1$–$C_6$-alkoxy, $R_5$ is hydrogen or halogen and A is a $C_2$–$C_6$-alkylene group or a salt of such compound. Preferably $R_1$ and $R_2$ are two equal $C_1$–$C_6$-alkyl groups or —$NR_1R_2$ is piperidino, pyrrolidino, morpholino, homopiperidino, piperazino or homopiperazino, $R_3$ is hydroxy, mercapto, $C_1$–$C_4$-alkoxy, $C_1$–$C_4$-alkylmercapto or $C_1$–$C_6$-alkylmino, mercapto, $C_1$–$C_6$-alkylmercapto, hydroxy or $C_1$–$C_6$-alkoxy and $R_5$ is hydrogen and salts thereof. The compounds are useful in treating ulcers and gastritis.

25 Claims, No Drawings

7-AZABENZIMIDAZOLES WITH BASIC SIDE CHAINS AND USE THEREOF

CROSS-REFERENCE TO RELATED APPLICATIONS

This application is a continuation-in-part of application Ser. No. 942,813, filed on Sept. 15, 1978, now abandoned, and application Ser. No. 947,528, filed on Oct. 2, 1978, now abandoned. The entire disclosure of the two parent applications is hereby incorporated by reference and relied upon.

BACKGROUND OF THE INVENTION

Compounds of the formula

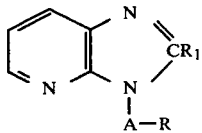

where the pyridine ring contains a nitro group, $R_1$ is hydrogen, halogen, an alkyl, alkony, alkylmercapto, hydroxy or mercapto group and A is a $C_1$–$C_5$-alkylene group and R is a dialkylamino group or a piperidino, pyrrolidino, piperazino or morpholino group are known. These compounds have a stimulating action on the central nervous system, especially an analeptic effect (Ciba French Pat. No. 1,290,128). While the French patent states that the nitro group containing compounds are of particular interest it does mention compounds on page 7, left column, second formula and in Example 15, wherein the pyridine ring is free of substituents and where R is dialkylamino. There is also generic disclosure of $R_1$ and R being defined as above in which the pyridine ring can be free of the nitro group. However, there are not disclosed any specific compounds in which $R_1$ is other than hydrogen and in which there is a substituent other than nitro on the pyridine ring. Also when a substituent is present on the pyridine ring, e.g., nitro, it is only shown meta to the pyridine nitrogen.

There are also known compounds of the formula

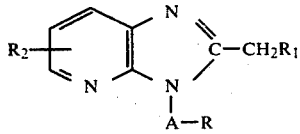

where A and R are as defined above and $R_1$ is phenyl or phenyl substituted by halogen, alkyl, alkoxy or alkylmercapto and $R_2$ is hydrogen, halogen, an alkyl or alkoxy group, an amino group or a nitro group. These compounds are stated to have an analgesic effect (Ciba French Pat. No. 1,273,372).

SUMMARY OF THE INVENTION

The present invention is directed to 7-azabenzimidazoles of the formula

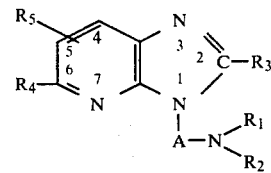

where $R_1$ and $R_2$ are the same or different and are hydrogen, $C_1$–$C_6$ alkyl or $C_2$–$C_6$ alkanoyl or —$NR_1R_2$ is a 5 to 7 membered saturated heterocyclic ring having either one nitrogen atom, one nitrogen atom and one oxygen atom or two nitrogen atoms, $R_3$ is hydroxy, an amino group, a mono $C_1$–$C_6$-alkylamino group, a di-$C_1$–$C_7$-alkylamino group, or a $C_2$–$C_6$ alkanoylamino group, $R_4$ is halogen, amino, mono $C_1$–$C_6$ alkylamino, di-$C_1$–$C_6$ alkylamino, mercapto, $C_1$–$C_6$-alkylmercapto, hydroxy or $C_1$–$C_6$-alkoxy, $R_5$ is hydrogen or halogen and A is a $C_2$–$C_6$ alkylene group or a salt of such compound. Preferably $R_1$ and $R_2$ are two equal $C_1$–$C_6$ alkyl groups or -$NR_1R_2$ is piperidino, pyrrolidino, morpholino, homopiperidino, piperazino or homopiperazino, $R_3$ is hydroxy, mercapto, $C_1$–$C_4$-alkoxy, $C_1$–$C_4$ alkylmercapto or $C_1$–$C_6$ alkyl and $R_4$ is halogen, amino, mono $C_1$–$C_6$ alkylamino, di-$C_1$–$C_6$ alkylamino, mercapto, $C_1$–$C_6$-alkylmercapto, hydroxy or $C_1$–$C_6$-alkoxy and $R_5$ is hydrogen and salts thereof. Most preferably $R_3$ is hydroxy, $R_5$ is hydrogen, $R_4$ is halogen or $C_1$–$C_4$ alkoxy; $R_1$ and $R_2$ are the same and are $C_1$–$C_4$ alkyl.

These compounds are new compounds, although some of them are within the broad language of French Pat. No. 1,290,128. The new compounds are useful in treating ulcers and gastritis as well as the other uses set forth subsequently. The uses of these compounds are completely different from those of the French patents.

In addition to the specific compounds mentioned in the working examples further compounds within the invention and useful for the purposes of the invention include for example:

1-(5-diethylaminopentyl)-2-hydroxy-6-chloro-7-azabenzimidazole;
1-(4-isopropylaminobutyl)-2-hydroxy-6-chloro-7-azabenzimidazole;
1-(2-dihexylaminoethyl)-2-hydroxy-6-chloro-7-aza-benzimidazole;
1-(2-dibutylaminoethyl)-2-hydroxy-6-chloro-7-aza-benzimidazole;
1-(2-methyl-2-amyl aminoethyl)-2-hydroxy-6-chloro-7-aza-benzimidazole;
1-(2-piperidinoethyl)-2-hydroxy-6-chloro-7-aza-benzimidazole;
1-(2-morpholinoethyl)-2-hydroxy-6-chloro-7-aza-benzimidazole;
1-(2-pyrrolidinoethyl)-2-hydroxy-6-chloro-7-aza-benzimidazole;
1-(2-homopiperidinoethyl)-2-hydroxy-6-chloro-7-azabenzimidazole;
1-(2-piperazinoethyl)-2-hydroxy-6-chloro-7-azabenezimidazole;
1-(2-homopiperazinoethyl)-2-hydroxy-6-chloro-7-azabenzimidazole;
1-(2-diacetylaminoethyl)-2-hydroxy-6-chloro-7-azabenzimidazole;
1-(2-propionylaminopropyl)-2-hydroxy-6-chloro-7-azabenezimidazole;
1-(2-caproylaminoethyl)-2-hydroxy-6-chloro-7-azabenzimidazole;

1-(2-dimethylaminoethyl)-2-acetylamino-6-chloro-7-aza-benzimidazole;
1-(2-diethylaminoethyl)-2-propionylamino-6-chloro-7-aza-benzimidazole;
1-(2-diethylaminoethyl)-2-caproylamino-6-chloro-7-aza-benzimidazole;
1-(2-diethylaminoethyl)-2-methylamino-6-chloro-7-aza-benzimidazole;
1-(2-diethylaminoethyl)-2-ethylamino-6-chloro-7-aza-benzimidazole;
1-(2-diethylaminoethyl)-2-dimethylamino-6-chloro-7-aza-benzimidazole;
1-(2-diethylaminoethyl)-2-diethylamino-6-chloro-7-aza-benzimidazole;
1-(2-diethylaminoethyl)-2-dihexylamino-6-chloro-7-aza-benzimidazole;
1-(2-diethylaminoethyl)-2-hydroxy-6-bromo-7-aza-benzimidazole;
1-(2-diethylaminoethyl)-2-hydroxy-6-fluoro-7-aza-benzimidazole;
1-(2-diethylaminoethyl)-2-hydroxy-6-amino-7-aza-benzimidazole;
1-(2-diethylaminoethyl)-2-hydroxy-6-ethylamino-7-aza-benzimidazole;
1-(2-diethylaminoethyl)-2-hydroxy-6-hexylamino-7-aza-benzimidazole;
1-(2-diethylaminoethyl)-2-hydroxy-6-diethylamino-7-aza-benzimidazole;
1-(2-diethylaminoethyl)-2-hydroxy-6-dibutylamino-7-aza-benzimidazole;
1-(2-diethylaminoethyl)-2-hydroxy-6-dihexylamino-7-aza-benzimidazole;
1-(2-diethylaminoethyl)-2-hydroxy-6-mercapto-7-aza-benzimidazole;
1-(2-diethylaminoethyl)-2-hydroxy-6-hexylmercapto-7-aza-benzimidazole;
1-(2-diethylaminoethyl)-2-hydroxy-6-butoxy-7-aza-benzimidazole;
1-(2-diethylaminoethyl)-2-hydroxy-6-n-hexoxy-7-aza-benzimidazole;
1-(2-diethylaminoethyl)-2-hydroxy-5,6-difluoro-7-aza-benzimidazole;
1-(2-diethylaminoethyl)-2-hydroxy-5,6-dibromo-7-aza-benzimidazole;
1-(2-diethylaminoethyl)-2-hydroxy-5-bromo-6-chloro-7-aza-benzimidazole;

The new compounds of the invention of formula I can be prepared by either (a) condensing to an imidazole ring a compound of the formula

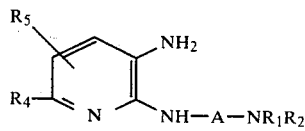

where A, $R_1$, $R_2$, $R_4$ and $R_5$ are as defined above with a compound of the formula $X=CYR_3$   III where X is oxygen, sulfur, $(OR_6)_2$ or $(SR_6)_2$ and $R_6$ is a $C_1$–$C_6$ alkyl group or where X is the group $=NR_7$ and $R_7$ is hydrogen or a $C_1$–$C_6$ alkyl group and Y is halogen, a hydroxy group, mercapto group, $C_1$–$C_6$ alkylmercapto group, an amino group, a mono or dialkylamino group wherein the alkyl is $C_1$–$C_6$ or the group  $COR_3$ where $R_3$ is as defined above or III is carbonyldiimidazole, $COCl_2$, or cyanogen halide, or (b) in a compound of formula I wherein $R_1$, $R_2$, $R_3$, $R_5$ and A are as defined above and $R_4$ is a nitro group, reducing this nitro group to an amino group and/or converting one or more of $R_1$, $R_2$, $R_3$, $R_4$, and $R_5$ into another group within its definition, and in a given case alkylating and/or acylating the compound obtained and in a given case converting the free base compound to its salt with an acid, preferably to the salt of a pharmaceutically acceptable acid.

Process (a) can be modified by first reacting a compound of formula II having an amino group in the 3-position with the compound of formula III to form an intermediate compound of the formula

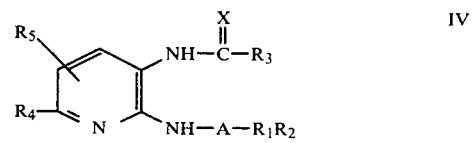

isolating this intermediate compound and subsequently converting it into a compound of formula I.

The compounds useful in the invention set forth above have the following unexpected activities, none of which are suggested by the above-mentioned French patents. They show for example a secretolytic, mucous thinning, stomach secretion retarding and protective activity against ulcers. Furthermore, they favor the formation of NANA (N-acetyl neuraminic acid in the mucous membrane of the stomach. Furthermore, they favor the healing of lesions and ulcers. The invention thus is also based on making available compounds with propitious pharmacodynamic properties which are valuable as medicines.

The groups $R_1$ to $R_5$, when they are defined as alkyl groups, alkanoyl groups, alkoxy groups, alkyl mercapto groups, mono alkyl and dialkylamino groups can be straight or branched chain. Likewise, the alkylene group A can be straight or branched. Especially the alkyl groups in the previously mentioned groups can consist of 1–4 carbon atoms, preferably 1, 2 or 3 carbon atoms, more preferably of 1 to 2 carbon atoms. The alkanoyl groups (definition of $R_1$, $R_2$ or in $R_3$) consists of, for example 2–5, preferably 2–4 carbon atoms, e.g. acetyl, propionyl, butyryl, valeroyl, or trimethylacetyl. The alkylene group A consists of particularly 2, 3 or 4, preferably 2 or 3 carbon atoms. In case $R_4$ and $R_5$ are halogen atoms, they are for example fluorine, chlorine or bromine (i.e. halogen of atomic weight 9 to 80), especially fluorine or chlorine. In case the group $—NR_1R_2$ forms a 5 to 7 membered heterocyclic ring, it is for example a pyrrolidino, piperidino, piperazino, homopiperazino, homopiperidino or morpholino ring.

Process (a)

The process can be carried out with or without a solvent (for example in a melt) at a temperature between 0° and 250° C. As solvents or suspension agents, there can be used for example water, saturated aliphatic alcohols (especially lower alcohols, e.g. methyl alcohol, ethyl alcohol, isopropyl alcohol, propyl alcohol, butyl alcohol, hexyl alcohol), aromatic hydrocarbons (e.g. toluene, xylene, benzene), halogenated aromatic hydrocarbons (e.g. 1,2,3-trichlorobenzene, 1,2,4-trichlorobenzene), aliphatic chlorinated hydrocarbons (e.g. tetrachloroethylene, methylene chloride, carbon tetrachloride, ethylene dichloride), dioxane, amides of aliphatic carboxylic acids (e.g. dimethyl formamide, dimethyl acetamide), dimethyl sulfoxide, pyridine, aliphatic glycols (e.g. ethylene glycol, propylene glycol, diethylene glycol, dipropylene glycol), phosphoric acid hexamethyltriamide. The compound of Formula III can likewise serve as solvent or suspension agent and in this case optionally is used in excess. In a given case, the reaction is carried out in the presence of a condensation agent. As this type of condensation agent there can be used for example mineral acids (sulfuric acid, phosphoric acid), inorganic acid halides (e.g. ($PCl_3$, $SOCl_2$, phosphorus oxychloride, phosphorus oxybromide), metal chlorides (e.g. zinc chloride), lower alkyl esters of phosphoric acid, e.g. trimethyl phosphate, triethyl phosphate, and tributyl phosphate, pyridine or salts of pyridine (for example with hydrohalic acids such as HCl), tertiary amines, e.g. triethylamine, alkali alcoholates, e.g. sodium ethylates. In case the compound of formula III represents an acid this can also be added in the form of its alkali metal (e.g. sodium or potassium) salt. In a given case, the reaction is carried out in such manner that the water formed in the condensation is distilled off simultaneously or subsequently in the presence of a solvent (e.g. xylene, trichlorobenzene, tetrachloroethylene or methylene chloride) which is not miscible with water. In case in the reactant III Y is the group $-O-COR_3$, Y especially means $C_1-C_6$-alkanoyloxy group, e.g. formoxy, acetoxy, propionoxy). For example, the compound III is the acid anhydride of an aliphatic $C_1-C_6$-carboxylic acids, e.g. acetic anhydride, propionic anhydride. As cyanogen halides, there can be used for example cyanogen bromide, cyanogen chloride or cyanogen iodide.

The process can in a given case also be carried out that an intermediate product of formula IV is isolated and then is subsequently cyclized.

The starting compounds of formula II can be obtained for example as follows: A 2-halogen-3-nitropyridine (2-chloro-3-nitro-pyridine or 2,5-dichloro-3-nitropyridine or 2,6-dichloro-3-nitropyridine) is reacted with an amine of the formula $H_2H-A-NR_1R_2$ in a polar solvent (aliphatic alcohols, e.g., those mentioned above, alcohol-water mixtures, dimethyl formamide, dioxane or even excess of the compound $R_1R_2N-A-NH_2$) with or without the addition of customary acid-binding additives at a temperature between 0° and 150° C., whereby the chlorine atom in the 2-position is exchanged. The thus obtained compound (formula II with a nitro group in place of $-NH_2$ in the 3-position) can either be directly reduced to the amine or formula II or in a given case there can be exchanged a chlorine atom in the 6- position to the group $R_4$. Then there subsequently takes place the reduction of the nitro group.

To produce the corresponding starting compounds which have a fluorine or bromine atom in the 6- position, for example the corresponding 3-nitro-6-chloropyridine which contains the group $-NH-A-NR_1R_2$ in the 2- position is heated with a saturated aqueous-alcoholic ammonia solution in an autoclave at 100° to 120° C. for several hours (2 to 4) and the 6-amino-pyridine derivative formed thereby then diazotized in known manner and caused to react according to the conditions of the Sandmeyer reaction or modified Sandmeyer reaction in the presence of fluoride or bromide ions and/or the corresponding copper (I) salt (CuBr, CuCl, CuF) or even fluoborate ions. As solvents there are suitable water-alcohol mixtures or mixtures of water, dimethyl formamide and dimethyl sulfoxide. For the production of the fluorine derivatives the dry diazonium fluoborate can also be thermally decomposed.

The exchange of chlorine or bromine (particularly in the 6- position) to other members within the definition of $R_4$ can take place by reaction with lower alkali alcoholates, e.g. sodium ethylate, alkali hydroxide, e.g. sodium hydroxide, potassium hydroxide, alkali sulfhydrides, e.g. sodium sulfhydride, ammonia or lower monoalkyl or dialkylamines, e.g. methyl amine, diethyl amine, whereby the corresponding compounds are obtained wherein $R_4$ is a $C_1-C_6$-alkoxy group, hydroxy group, mercapto group, amino group, mono-$C_1-C_6$-alkylamino or di-$C_1-C_6$-alkylamino group. These reactions as a rule are carried out in alcohols, e.g. methanol, ethanol or isopropanol, or tetrahydrofurane, in a given case with an excess of the basic components at a temperature between 0° and 250° C. Those compounds where $R_4$ is an alkylmercapto group are obtained from the corresponding mercapto compounds by customary alkylation. Starting compounds in which $R_4$ or $R_5$ is a bromine atom can also be made from the corresponding compounds in which $R_4$ or $R_5$ is OH by brominating with a brominating agent such as $POBr_3$, $PBr_5$, or $SOBr_2$, in a given case in an inert medium between 20° and 200° C. The production of starting compounds wherein $R_4$ or $R_5$ is F can also take place in a modified manner in which there is gradually added $NaNO_2$ at a temperature between 0° and 50° C. to a solution in concentrated aqueous hydrofluoric acid of the corresponding compounds where $R_4$ or $R_5$ is an amino group, or a slow stream of nitrous gas can be led in.

The reduction of the nitro group in the three position takes three by known methods, for example catalytically with Raney-nickel, platinum or palladium catalysts in solvents such as alcohol, dioxane, dimethyl formamide, etc. at hydrogen pressures between 1 and 100 bar or with reducing agents such as iron/hydrochloric acid, tin (II) chloride, titanium trichloride, $LiAlH_4$ or their modified products (partial alcoholysis products), in solvents such as water, aliphatic alcohols, e.g. methanol, ethanol, isopropanol, toluene, dioxane, tetrahydrofurane or ethylene glycol ethers, e.g. methoxyethanol, at temperatures between ) and 100° C.

Compounds of formula II where $R_4$ is an amino group can also be obtained through the reduction of dinitropyridine compounds (with the residue $-NH-A-NR_1-R_2$ in the 2- position) by methods corresponding to the previously mentioned reductions.

Starting compounds of formula II wherein $R_4$ and/or $R_5$ is a halogen atom, for example, can also be obtained from compounds of formula II wherein $R_4$ and/or $R_5$ is hydrogen by introducing a chlorine or bromine atom by nucleophilic reaction. This occurs for example with alkali salts, e.g. the sodium or potassium salt of chloric acid or bromic acid in the presence of a strong mineral acid (HCl or HBr) at a temperature between 0° and 50° C.

Process (b)

In the case where $R_4$ is a halogen atom, for example chlorine or bromine, then such a halogen atom can be exchanged with a hydroxy or mercapto or alkoxy or alkylmercapto or an amino or a substituted amino group as defined in connection with formula I. For this purpose a compound of formula I wherein $R_4$ is a halogen atom is reacted with ammonia or an ammonia yielding compound (hexamethylenetetramine, ammonium carbonate, alkaliamide, e.g. sodamide, or ammonium salts of weak acids) or an alkylamine with 1–6 carbon atoms or a dialkylamine with an alkyl residue of 1–6 carbon atoms, e.g. methylamine, ethylamine, hexylamine, dimethylamine, diethylamine, dihexylamine. This reaction can be carried out for example in an inert solvent or suspension agent such as tetrahydrofurane, dioxane, ethanol, n-propanol, dimethyl sulfoxide or dimethyl formamide or even in the presence of an excess of the basic reactant at temperatures between 0° and 200° C., preferably 40° to 130° C. For this purpose there can be added acid acceptors such as potassium carbonate, sodium bicarbonate, calcium carbonate, non-quarternized tertiary amines such as diisopropyl-methylamine or even basic ion exchangers.

The exchange of halogen with the hydroxy group takes place for example in alcoholic or aqueous-alcoholic medium between 20° and 150° C. with addition of a metal hydroxide such as NaOH, KOH, AgOH (or $Ag_2O$) or other alkaline reacting salts such as potassium carbonate or sodium carbonate. In the case of exchange with a mercapto group, it is recited with a sulfide, especially alkali sulfide, e.g. sodium sulfide, or alkaline earth sulfide, e.g. calcium sulfide as stated above.

In the case of the exchange with alkoxy or alkylmercapto groups, the reaction is carried out by reaction with the corresponding alcohol or alkyl mercaptan in, for example, a polar solvent such as an alcohol or acetone with addition of an acid binding agent such as an alkali, e.g. sodium hydroxide, tertiary amine, e.g. triethylamine, or even silver oxide. The alcohol is preferably used in excess. Preferably the temperature is between 20° and 150° C. In the case of the exchange of $R_4$=halogen with the above mentioned groups, the temperature is preferably between 0° and 50° C. In essence, for all of the exchange reactions set forth here, there can also be used all of the acid binding agents mentioned in connection with the reactions with amines.

In the case where $R_4$ is an amino group such an amino group can be exchanged with a hydroxy group or a halogen atom. This reaction takes place for example in aqueous, alcoholic or aqueous/alcoholic medium at temperatures between 0° and 100° C. in the presence of an acid, e.g. hydrochloric acid, and with addition of an alkali nitrite e.g. sodium nitrite, alkyl nitrite, e.g. butyl nitrite, or $N_2O_3$ (or nitrous gases). In the case of the exchange with halogen, there is used an excess of the acid involved or concentrated hydrofluoric acid or the action of the halogenating agent takes place for example in combination with a diazotization (Sandmeyer reaction or modified Sandmeyer process) in the presence of the corresponding halogen ions and/or corresponding copper (I) salts or even fluoroborate ions.

In the case where $R_4$ is a hydroxy group or an alkoxy group then such a group can be exchanged with a halogen atom. This reaction is carried out in inert solvents such as dioxane, chloroform, hydrocarbons such as benzene, toluene or even nitrobenzene, diethyl ether, acetone, dimethyl formamide, ethylene dichloride with halogenating agents such as phosphorus pentachloride, phosphorus oxychloride, thionyl chloride, titanium tetrachloride, triphenylphosphine dichloride or even halophosphoric acid esters such as diethoxyphosphoric trichloride at temperatures between 20° and 150° C.

Furthermore, it is possible in compounds of formula I wherein $R_5$ is a halogen atom (especially Cl or Br) to replace this halogen atom by hydrogen. This reduction takes place for example in a solvent or suspension agent (lower alcohols, water, dioxane, acetic acid) with hydrogen in the presence of noble metal catalysts at temperatures between 0° and 100° C. and pressures between 1 and 100 bar.

In compounds of formula I wherein $R_5$ is hydrogen and the remaining symbols have the stated meanings chlorine or bromine can be introduced. This action takes place, for example, with alkali salts of chloric acid or bromic acid in the presence of strong mineral acids (HCl, HBr) at temperatures between 0° and 50° C.

The reduction of compounds of formula II wherein $R_4$ is a nitro group takes place for example catalytically with Raney-nickel, platinum or palladium catalysts in solvents such as alcohols, dioxane, dimethyl formamide, etc. at hydrogen pressures between 1 and 100 bar or with reducing agents such as iron/hydrochloric acid, tin (II) chloride, titanium trichloride, $LiAlH_4$ or their modifications (partial alcoholysis products), in solvents such as water, aliphatic alcohols, toluene, dioxcine, tetrahydrofurane or ethylene glycol ethers at temperatures between 0° and 100° C. The amino group thus obtained can then, as mentioned above, be further transformed.

Especially process (b) consists of reacting a compound of formula I wherein $R_4$ is chlorine or bromine and the remaining symbols have the above given meanings with a compound of the formula H-T or its alkali salt where T is a hydroxy or mercapto group, a $C_1$–$C_6$-alkylmercapto group, a $C_1$–$C_6$ alkoxy group, an amino group, a mono $C_1$–$C_6$ alkylamino group or a di $C_1$–$C_6$ alkylamino group or in a compound of formula I a halogen atom, $R_5$-halogen, of the pyridine ring is reductively split off or there is introduced chlorine or bromine into a compound of formula I wherein $R_5$ is hydrogen.

The products of the process can optionally be alkylated, for example compounds of formula I, wherein $R_3$ is an amino group. Likewise compounds wherein $R_1$ and/or $R_2$ is hydrogen can be connected into the corresponding mono or dialkylamino compounds by alkylation. Furthermore compounds of formula I wherein $R_4$ is an amino group, a hydroxy or a mercapto group can be alkylated to compounds wherein $R_4$ is a mono or dialkylamino group or an alkoxy or alkylmercapto group. These alkylations take place in a manner known as of itself. As alkylation agents there can be used for examples esters of the formula alkyl halide, e.g. methyl chloride, methyl bromide, ethyl chloride, $ArSO_2O$ alkyl, e.g. methyl p-toluenesulfonate and $SO_2(OA\ alkyl)_2$ wherein Hal is a halogen atom (especially chlorine, bromine or iodine) and Ar is an aromatic group, as for example a phenyl or naphthyl group which in a given case can be substituted by one or more lower alkyl groups and where alkyl is an alkyl group of 1–6 carbon atoms. Examples are p-toluenesulfonic acid $C_1$–$C_6$ alkyl esters, e.g. ethyl p-toluene-sulfonate, methyl-p-toluenesulfonate, hexyl p-toluenesulfonate, lower $C_1$–$C_6$-dialkyl sulfates, e.g. dimethyl sulfate, dibutyl sulfate, diethyl sulfate and the like. The alkylation reaction is undertaken in a given case with addition of customary acid binding agents, such as alkali carbonates, e.g. sodium or potassium carbonate, pyridine or other customary tertiary amines, at temperatures between 0° and 150° C. in inert solvents such as alcohols, dioxane, dimethyl formamide, dimethyl sulfoxide, aromatic hydrocarbons such as benzene or toluene or acetone.

In a given case there can also be provided in the alkylation that first there is produced from the compound to be alkylated an alkali metal compound while it is reacted in an inert solvent such as dioxane, dimethyl formamide, benzene or toluene with an alkali metal, alkali hydride or alkaliamide (especially sodium or sodium compounds) at temperatures between 0° and 150° C. and then the alkylating agent added (for example in the case wherein the starting compound $R_3$ is hydrogen.

Products of the process of formula I wherein $R_3$ is an amino group and/or $R_1$ is hydrogen, $R_2$ is hydrogen or a $C_1$–$C_6$ alkyl group can be acylated on the $NH_2$- group or the group —$NR_1R_2$ by an alkanoyl group of 2–6 carbon atoms.

This acylation can take place in inert solvent or suspension agents such as dioxane, dimethyl formamide, benzene or toluene at temperatures between 0° and 200° C., preferably 20° to 150° C. As acylating agents there can be used ketone as well as acid halides (chloride, bromide, iodide, e.g. acetyl chloride, propionyl bromide, butyryl iodide), acid anhydrides, e.g. acetic anhydride, or acid esters of aliphatic carboxytic acids with 2–6 carbon atoms, in a given case with the addition of an acid binding agent such as alkali carbonates, alkali hydroxides, alkali alcoholates or a tertiary amine, for example triethylamine. In regard to the esters there are particularly used those with lower aliphatic alcohols, e.g. methanol or ethanol. In the acylation it can also be provided that first an alkali metal compound is produced from the compound to be reacted while the reaction is carried out with an alkali metal, alkali hydride or alkaliamide (particularly sodium or sodium compounds) in an inert solvent such as dioxane) dimethyl formamide, benzene or toluene at temperatures between 0° and 150° C. and then to add the acylating agents.

In a given case the acylating agent can also be used in excess. It is also possible in many cases to acylate directly with an aliphatic carboxylic acid of 2–6 carbon atoms (e.g. an alkanoic acid, e.g. acetic acid) with addition of the corresponding condensation agent as, for example, dicyclohexylcarbodiimide or for example 1-ethyl-2-ethoxycarboxyldihydroquinoline.

In place of the alkylating and acylating agents mentioned there can also be used other agents used as the equivalents thereof (see for example L. F. and Mary Fieser "Reagents for Organic Synthesis", John Wiley and Sons, Inc. New York, 1967, Vol. 1, pages 1303–1304 and Vol 2, page 471). Of course acyl groups present in compounds of formula I can also be split off again in known manner.

It is also possible in the alkylation to protect by previous acylation with customary acid derivatives individual, functionally acylatable groups. Thus, such groups are protected by customary protective groups. Such protective groups can then be split off again in known manner. This splitting off takes place for example in aqueous, aqueous alcoholic media or even in mixtures of acetone with water and/or alcohols or even in pure alcohols in the presence of alkali such as potassium hydroxide, sodium ethylate, potassium carbonate or even tertiary amines or secondary or primary amines wherein these materials are present preferably in equivalent amounts. The splitting off can also take place in low molecular weight alcohols with addition of small amounts of strong acids (hydrochloric acid, sulfuric acid) p-toluenesulfonic acid). The temperatures for the splitting off of the acyl groups generally lie between 0° and 150° C.

Basic compounds of formula I can be converted into their salts in known manner. As anions for these salts there can be used the theropeutically (or pharmaceutically) usable acid residues to form pharmaceutically compatible acid addition salts. Examples of such acids are sulfuric acid, phosphoric acid, hydrohalic acids, e.g., hydrochloric acid and hydrobromic acid, ethylenediaminetetraacetic acid, sulfamic acid, benzenesulfonic acid, p-toluenesulfonic acid, camphorsulfonic acid, methanesulfonic acid, guaiazulic sulfonic acid, maleic acid, fumaric acid, oxalic acid, tartaric acid, lactic acid, ascorbic acid, glycolic acid, salicylic acid, acetic acid, propionic acid, gluconic acid, benzoic acid, citric acid, acetaminoacetic acid, hydroxyethane sulfonic acid.

In customary manner the free bases can again be produced from the salts of the compounds, for example by treating a solution in an organic medium such as an alcohol (e.g., methanol) with soda or caustic soda solution.

Compounds of formula I can also be present in tautomeric forms, wherein they can then be present entirely or partially in one of the possible tautomeric forms. Generally under the normal working and storage conditions an equilibrium is present.

Those compounds of formula I which contain asymmetrical carbon atoms and as a rule accumulate as a racemate can be split in known manner, for example with the help of an optically active acid into the optically active isomers. However, it is also possible to add an optically active starting material beforehand whereby as the final product a corresponding optically active or diastereomeric form is then obtained.

The compounds of the invention are suited for the production of pharmaceutical compositions. The pharmaceutical compositions or medicaments can contain one more of the compounds of the invention or even mixtures of the same with other pharmaceutically active materials. For the production of pharmaceutical preparations there can be used the customary pharmaceutical carriers and assistants. The medicines can be employed internally, parenterally, orally or perlingually. For example dispensation can take place in the form of tablets, capsules, pills, dragees, plugs, salves, jellies, creams, powders, liquids, dusts or aerosals. As liquids there can be used for example oily or aqueous solutions or suspensions, emulsions, injectable aqueous and oily solutions or suspensions.

The compounds according to the invention are suitable for the production of pharmaceutical compositions and preparations. The pharmaceutical compositions or medicaments contain, as active principle, one or more of the compounds according to the invention, optionally in admixture with other pharmacologically or pharmaceutically active substances. The medicaments may be prepared with the usual pharmaceutical excipients, assistants, carriers, and diluents.

As carriers and assistants, for example, are those recommended in the following literature as adjuvants for pharmacy, cosmetic and related fields such as in Ullmann's Encyklopädie der technischer Chemie, Vol. 4 (1953), pages 1 to 39; Journal of Pharmaceutical Sciences 52 (1963), pages 918 et seq.; N. v. Czetsch-Lindenwald, Hilftstoffe fur Pharmazie und angrenzende Gebiete; Pharm. Ind. 2 (1961), pages 72 et seq.; Dr. H. P. Fiedler, Lexicon der Hilftstoffe fur Pharmazie, Kosmetik und angrenzende Gebiete, Cantor Kg. Aulendorf i. Wurtt (1971).

Examples of such materials include gelatin, natural sugars such as sucrose or lactose, lecithin, pectin, starch (for example conrstarch), alginic acid, tylose, talc, lycopodium, silica (for example colloidal silica), glucose, cellulose, cellulose derivatives for example cellulose ethers in which the cellulose hydroxyl groups are partially etherified with lower aliphatic alcohols and/or lower saturated oxyalcohols (for example methyl hydroxypropyl cellulose, methyl cellulose, hydroxyethyl cellulose), stearates, e.g., methylstearate and glyceryl stearate, magnesium and calcium salts of fatty acids with 12 to 22 carbon atoms, especially saturated acids (for example calcium stearate, calcium laurate, magnesium oleate, calcium palmitate, calcium behenate and magnesium stearate), emulsifiers, oils and fats, especially of plant origin (for example peanut oil, castor oil, olive oil, sesame oil, cottonseed oil, corn oil, wheat germ oil, sunflower seed oil, cod-liver oil), mono-, di- and triglycerides of saturated fatty acids ($C_{12}H_{24}O_2$ to $C_{18}H_{36}O_2$ and their mixtures), e.g., glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400 and other polyethylene glycols, as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atom alkanols) or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case also be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane), magnesium carbonate and the like.

For the production of solutions there can be used water or physiologically compatible organic solvents, as for example, ethanol, 1,2-propylene glycol, polyglycols, e.g., diethylene glycol, triethylene glycol and dipropylene glycol and their derivatives, dimethyl sulfoxide, fatty alcohols, e.g., stearyl alcohol, cetyl alcohol, lauryl alcohol and oleyl alcohol, triglycerides, e.g., glyceryl oleate, glyceryl stearate, glyceryl palmitate, and glyceryl acetate, partial esters of glycerine, e.g., monoacetic, diacetin, glyceryl monostearate, glyceryl distearate, glyceryl monopalmitate, paraffins and the like.

In the production of the preparations there can be used known and customary solution aids or emulsifiers. As solution aids and emulsifiers there can be used, for example, polyvinyl pyrrolidone, sorbitan fatty acid esters such as sorbitan trioleate, lecithin, gum acacia, gum tragacanth, polyoxyethylated sorbitan monoleate, polyoxyethylated fats, polyoxyethylated oleotriglycerides, linolized oleotriglycerides, polyethylene oxidecondensation products of fatty alcohols, alkylphenols or fatty acids. As used herein polyoxyethylated means that the materials in question contain polyoxyethylene chains whose degree of polymerization generally is between 2 and 40, particularly between 10 and 20.

Such polyoxyethylated materials for example can be obtained by reaction of hydroxyl group containing compounds (for example mono- or diglycerides) or unsaturated compounds such as, for example, those containing the oleic acid radical with ethylene oxide (for example 40 moles of ethylene oxide per mole of glyceride).

Examples of oleotriglycerides are olive oil, peanut oil, castor oil, sesame oil, cottonseed oil, corn oil (see also Dr. H. P. Fiedler, supra, pages 191-195).

Furthermore, there can be added preservatives, stabilizers, buffers, for example, calcium hydrogen phosphate, colloidal aluminum hydroxide, taste correctives, antioxidants and complex formers (for example ethylene diamine tetraacetic acid) and the like. In a given case for stabilization of the active molecular the pH is adjusted to about 3 to 7 with physiologically compatible acids or buffers. Generally, there is preferred as neutral as possible to weak acid (to pH 5) pH value. As antioxidants there can be used for example sodium metal bisulfate, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example lower alkyl esters such as the methyl ester and the ethyl ester) benzoic acid, sodium benzoate, trichloroisobutyl alcohol, phenol, cresol, benzethonium chloride and formalin derivatives).

The pharmacological and galenical treatment of the compounds of the invention takes place according to the usual standard method. For example, the active material or materials and assistants or carriers are well mixed by stirring or homogenization (for example by means of a colloid mill or ball mill), wherein the operation is generally carried out at temperatures between 20° and 80° C., preferably 20° to 50° C.

The application of active material or drug can take place on the skin or mucous membrane or internally, for example, orally, enterally, rectally, introvenously, intromuscularly, intraperitoneally, or subcutaneously.

The addition of other medicines, especially hydrogen antagonists, carbenoxolone, antacids or spasmolytics is also possible or favorable.

The compounds of the invention on experimental ulcer patterns show a good anti-ulcerogenic activity. For example in the above mentioned test methods there is produced at a dosage of 3 mg/kg of body weight (kg rat) a 50% antiulcerogenic activity.

This antiulcerogenic activity is comparable with the action of the known medicine Cimetidine or with the carbenoxolones.

The lowest effective dosage in the above mentioned animal experiment is for example 10 mg/kg introvenously, for example, 50 mg/kg orally. The lowest effective dosage was determined on the acetic acid ulcer model as described in Takagi, Jap. J. Pharmac., Vol. 19, pages 418 to 426 (1969).

As the general dosage range for the activity (animal experiments as above) there can be used for example 1 to 50 mg/kg orally; 0.1 to 50 mg/kg, intravenously. The general dosage range was determined by the ethanol ulcer model as described by Goldenberg, Gastroenterology, Vol. 69, pages 636–640 (1975).

The compounds of the invention are indicated for use in ulcus ventriculi, ulcus duodeni, gastritis, stomach irritation, Zollinger-Elison syndrome, and reflux oesophagitis.

The pharmaceutical preparations generally contain between 100 to 200 mg of the active component or components of the invention.

The compounds can be delivered in the form of tablets, capsules, pills, drageés, plugs, salves, gels, creams, powders, dusts, aerosols or in liquid form. As liquid forms there can be used for example oily or alcoholic or aqueous solutions as well as suspension and emulsions. The preferred forms of use are tablets which contain between 100 and 200 mg or solutions which contain between 0.1 and 0.2% of active material.

In individual doses the amount of active component of the invention can be used for example in an amount of:

a. in oral dispensation between 100 and 200 mg;
b. in parenteral dispensation (for example intravenously, intramuscularly) between 100 and 200 mg;
c. in dispersion for rectal or vaginal applications between 200 and 500 mg.

For example, there is recommended the use of 1 to 2 tablets containing 100 to 200 mg of active ingredient 3 times daily or for example, intravenously the injection 1 to 2 times daily of a 2 to 5 ml ampoule containing 100 to 200 mg of active substance. In oral preparations the minimum daily dosage for example is 600 mg; the maximum daily dosage in oral administration should not be over 2000 mg.

The dosages in each case are based on the free base.

The acute toxicity of the compounds of the invention in the mouse (expressed by the $LD_{50}$ mg/kg method of Miller and Tainter, Proc. Soc. Exper. Biol. and Med. 57 (1944), pages 261 et seq.) in oral application is between 500, g/kg and 700 mg/kg.

The drugs can be used in human medicine, in veterinary medicine as well as in agriculture alone or in admixture with other pharmacologically active materials. The compounds can be used to treat dogs and cats.

The compositions can comprise, consist essentially of or consist of the materials set forth.

The methods can comprise, consist essentially of or consist of the steps set forth with the materials shown.

DESCRIPTION OF THE PREFERRED EMBODIMENTS

EXAMPLE 1

1-(2-Diethylaminoethyl)-2-hydroxy-6-chloro-7-aza-benzimidazole

The solution of 80 grams of 2-(2-diethylaminoethylamino)-3-amino-6-chloropyridine in 900 ml of dioxane was treated with stirring with 32 ml of pyridine and 36.6 ml of ethyl chloroformate and stirred for one hour. The product precipitating thereby was washed with water and dried (2-(2-diethylaminoethylamino)-3-carbethoxy-amino-6-chloropyridine, M.P. 205°–206° C.) and subsequently melted with occasional stirring and held for 3 hours at 190°–210° C. After cooling the solidified melt was recrystallized from methanol under the addition of activated carbon and isopropanolic H Cl. M.P. of the hydrochloride 252°–254° C.; Yield 52.8 grams.

Production of the Starting Material

To a mixture of 250 grams of 2,6-dichloro-3-nitropyridine, 100 grams of potassium carbonate and 1.5 liters of ethanol there were dropped in with stirring at room temperature 180 grams of N,N-diethylethylenediamine. Thereupon the temperature increased temporarily to 40° C. It was stirred in all for 2 hours, then the precipitated yellow 2-(2-diethylaminoethylamino)-3-nitro-6-chloropyridine filtered off with suction, thoroughly washed with water and recrystallized from ethanol. M.P. 52°–53° C. (Yield: 234 grams).

90 grams of this nitro compound were then hydrogenated in 900 ml of dioxane at 80 bar and 50° C. under addition of 40 grams of Raney-nickels and 100 grams of magnesium sulfate. After the end of the reaction the hydrogenating solution was freed from catalyst under a nitrogen atmosphere. The thus obtained filtrate can be used directly for the reaction with formation of the benzimidazole ring.

EXAMPLE 2

1-(2-acetylaminoethyl)-2-hydroxy-6-chloro-7-aza-benzimidazole

Production of the title compound took place in an analogous manner to Example 1 by reaction of 9.9 ml of ethyl chloroformate with the hydrogenation solution from 25.8 grams of 2-(2-acetyl-aminoethylamino)-3-nitro-6-chloropyridine. The precipitated product was cyclized in a manner analogous to that of Example 1 by melting at 200°–220° C. and the reaction product recrystallized from methanol with addition of activated carbon.

Yield: 5.5 grams; M.P. 221°–222° C.

EXAMPLE 3

1-(2-Diethylaminoethyl)-2-hydroxy-6-methylamino-7-aza-benzimidazole 27 grams of 2-(diethylaminoethylamino)-3-nitro-6-methylamino pyridine were hydrogenated in dioxane in a manner analogous to Example 1 and the hydrogenation solution reacted with 9.9 ml of ethyl chloroformate, whereby 13.8 ml of triethylamine were added. After 2 hours the triethylamine hydrochloride was filtered off with suction from the reaction mixture, washed with dioxane and the filtrate evaporated in a vacuum. The residue was heated under nitrogen to 180° C. After 8 hours 90% of the substance cyclized (thin layer chromatography). The thus obtained reaction product was chromatographed on silica gel (running agent 95% chloroform, 4% methanol, 1% aqueous ammonia). The zone of the column which contained the desired substance was cut out, eluted with methanol and the eluate concentraded. There were obtained from the residue by digestion with etyly acetate 4 grams of pure, crystalline title substance, M.P. 116°–118° C.

EXAMPLE 4

1-(2-Diethylaminoethyl)-2-hydroxy-6-methoxy-7-aza-benzimidazole

The filtrated hydrogenation solution from 28 grams of 2-(diethylaminoethylamino)-3-nitro-6-methoxypyridine in 450 ml of dioxane (10 grams Raney nickel, 50 bar and 65° C.) were treated under stirring with 11.25 grams of ethyl chloroformate. After 3 hours stirring the open carbethoxy compound was filtered off and heated to 180° C. under stirring and held at this temperature for one hour. The cooled melt was recrystallized from isopropanol.

Yield: 7.6 grams, M.P. 216°–217° C.

EXAMPLE 5

1-(2-Diethylaminoethyl)-2-hydroxy-6-ethoxy-7-aza-benzimidazole.

The title compound was produced in a manner analogous to Example 4 starting from 20 grams of 2-(diethylaminoethylamino)-3-nitro-6-ethoxypyridine and 8 grams of ethyl chloroformate. The base was dissolved in acetone and by addition of 30% ethanolic H Cl the hydrochloride produced, which crystallized pure.

Yield: 10 grams M.P. of the hydrochloride 184°–186° C.

EXAMPLE 6

1-(2-Diethylaminoethyl)-2-hydroxy-6-n-propoxy-7-aza-benzimidazole.

The compound was produced in a manner analogous to Example 4 (or Example 5) starting from 36 grams of 2-(diethylaminoethylamino)-3-nitro-6-n-propoxypyridine and 13.5 grams of ethyl chloroformate produced. Yield: 24 grams M.P. of the hydrochloride 210°–212° C.

EXAMPLE 7

1-(3-Diethylaminopropyl)-2-hydroxy-6-chloro-7-aza-benzimidazole.

The production was carried out in a manner analogous to Example 1 from 20 grams of 2-(3-diethylaminopropylamino)-3-amino-6-chloropyridine and 9 ml of ethyl chloroformate. M.P. of the hydrochloride of the title compound was 203°–205° C.; yield: 14 grams.

EXAMPLE 8

1-(2-Diethylaminoethyl)-2-hydroxy-6-dimethylamino-7-aza-benzimidazole.

A solution of 59 grams of 2-(2-diethylaminoethylamino-6-dimethylaminopyridine in 900 ml of dioxane were treated under stirring with 22 ml of pyridine and 27 ml of ethyl chloroformate, stirred for one hour, evaporated in vacuum and the residue heated for two hours up to 190° C. After the cooling off the product was recrystallized from isopropanol with addition of activated carbon. There was obtained the reaction product as the hydrochloride having an M.P. of 166°–169° C.; Yield: 10.5 grams.

Production of the Starting Substance

There were introduced 67 grams of gaseous dimethylamine into a solution of 70 grams of 2-(2-diethylaminoethylamino)-3-nitro-6-chloropyridine in 350 ml n-propanol. After 2 hours the solution was concentrated in a vacuum and the evaporation residue as described in Example 1 reduced in the presence of Raney nickel.

EXAMPLE 9

1-(2-diethylaminoethyl)-2-hydroxy-6-methylmercapto-7-aza-benzimidazole 29 grams of 2-(2-diethylaminoethylamino)-3-amino-6-methylmercapto-pyridine (crude product) were mixed with 25 grams of 1,1'-carbonylidiimidazole and the mixture heated under stirring to 130° C. After 15 minutes it was cooled and the warm melt stirred up with water.

The base which crystallized out was filtered off with suction. The base was precipitated from a solution in isopropanol by addition of 30% isopropanolic H Cl. The hydrochloride was recrystallized from ethanol. Yield: 12 grams; M.P. of the hydrochloride 206°–208° C.

Production of the Starting Material 30 grams of 2-(2-diethylaminoethylamino)-3-nitro-5-methylmercaptopyridine in 300 ml of tetrahydrofurane were treated with stirring with 23 grams of activated aluminum powder, whereupon the temperature increased to 60° C. After cooling it was stirred for another 30 minutes at room temperature, the aluminum hydroxide filtered off with suction and the filtrate evaporated to dryness in a vacuum. The product thus obtained was directly worked up further.

EXAMPLE 10

1-(2-Morpholinoethyl)-2-hydroxy-6-methoxy-7-aza-benzimidazole.

18 grams of 2-morpholinoethylamino-3-nitro-6-methoxypyridine were hydrogenated and further reacted in an anlogous manner to Example 1. The hydrogenation solution after removal of the catalyst by suction filtering evaporated in a vacuum and the syrupy residue stirred with 24 grams of 1,1'-carbonyldiimidazole. After one hour the melt was treated with water and ethyl acetate, the organic phase washed with water, dried and concentrated. The base crystallized and was recrystallized from ethanol. The hydrochloride was produced from it in acetone by addition of 20% ethanolic H Cl. Yield: 5 grams; M.P. of the hydrochloride 242°–244° C.

EXAMPLE 11

1-(2-Diethylaminoethyl)-2-amino-6-methoxy-7-azabenzimidazole.

The reaction solution obtained by hydrogenation of 60 grams of 2-(2-diethylaminoethylamino)-3-nitro-6-methoxypyridine in 450 ml of ethanol with 20 grams of Raney nickel at 50 bar and 40°–50° C. was filtered off from the catalyst and the filtrate treated with 26 grams of cyanogen bromide under stirring. The temperature increased to 40° C. Then the mixture was stirred further for 3 hours at this temperature. It was allowed to stand overnight, the precipitated product filtered off with suction and washed with ethanol. The crude product was dissolved in water, made alkaline with ammonia, the oily base crystallized after some time. It was filtered off with suction, washed, dissolved in isopropanol and treated with 20% isopropanolic hydrochloric acid. The precipitated hydrochloride was recrystallized from ethanol. Yield: 18 grams; M.P. of the hydrochloride 265°–270° C.

EXAMPLE 12

1-(2-Diethylaminoethyl)-2,6-dihydroxy-7-aza-benzimidazole.

10 grams of 1-(2-diethylaminoethyl)-2-hydroxy-6-methoxy-7-aza-benzimidazole were boiled for 5 hours at reflux in 100 ml of 48% hydrobromic acid and the solution evaporated in a vacuum. The residue was stirred with isopropanol, filtered with suction and then recrystallized twice from ethanol under the addition of activated carbon.

EXAMPLE 13

1-(2-Aminoethyl)-2-hydroxy-6-chloro-7-aza-benzimidazole.

11 grams of 1-(2-acetylaminoethyl)-2-hydroxy-6-chloro-7-aza-benzimidazole were stirred for 4 hours with 40 ml of concentrated hydrochloric acid at 80° C. and allowed to stand overnight at 0° C., the substance crystallized out was recrystallized from methanol. Yield: 5 grams; M.P. of the hydrochloride 310°–312° C.

EXAMPLE 14

1-(2-N-methylaminoethyl)-2-hydroxy-6-chloro-7-aza-benzimidazole.

5.2 grams of 1-(2-N-acetyl-N-methylaminoethyl)-2-hydroxy-6-chloro-7-aza-benzimidazole were heated to 90° C. in 20 ml of concentrated hydrochloric acid for 90 minutes. After cooling the precipitated material was filtered off with suction and washed with methanol. Yield: 2.4 grams; M.P. of the hydrochloride 344°–346° C.

EXAMPLE 15

1-(2-N-acetyl-N-methylaminoethyl)-2-hydroxy-6-chloro-7-aza-benzimidazole.

21 grams of 1-(2-acetylaminoethyl)-2-hydroxy-6-chloro-7-aza-benzimidazole were dissolved in 150 ml of dimethyl formamide, then there were added in portions at room temperature under stirring 2.64 grams of sodium hydride (80% in white oil), the mixture stirred for a further half hour and there 11.4 grams of methyl iodide dropped in. After 3 hours the precipitated sodium iodide was filtered off with suction, the filtrate concentrated in a vacuum, and the residue treated with water. The precipitated material was washed with water. Yield: 8 grams; M.P. 166°–167° C.

EXAMPLE 16

1-(2-Diethylaminoethyl)-2-hydroxy-5,6-dichloro-7-aza-benzimidazole.

15 grams of 1-(2-diethylaminoethyl)-2-hydroxy-6-chloro-7-aza-benzimidazole were dissolved in 200 ml of concentrated hydrochloric acid and there were added in portions with stirring 24.5 grams of potassium chlorate at room temperature. The temperature increased temporarily to 33° C. The mixture was stirred for another hour, made alkaline with sodium hydroxide, the mixture extracted with shaking with n-butanol, the extract evaporated in a vacuum and the residue chromatographed over silica gel. The reaction product was recrystallized from ethyl acetate. M.P. 137°–139° C.; Yield: 3 grams.

EXAMPLE 17 (Capsules)

To prepare 100,000 capsules there were required the following new materials:

| Compound of Example 1 | 0.5 kg |
|---|---|
| Lactose | 33.0 kg |
| Microcrystalline cellulose | 10.0 kg |
| Highly dispersed silica | 0.5 kg |
| Magnesium stearate | 2.0 kg |
| | 45.0 kg |

Production

The total raw materials which were necessary for production of the capsule composition were passed through a sieve having a mesh width of 1.5 mm and subsequently were mixed for 1 hour at 10 revolutions per minute in a mixer. This composition is called the capsule filling composition.

The capsule filling composition was filled into 100,000 gelatin capsules of size 0.

Amount of filling per capsule: 450 mg.

EXAMPLE 18

Tablets

To make 1,200,000 tablets there were required:

| Compound of Example 1 | 6.0 kg |
|---|---|
| Microcrystalline cellulose | 60.0 kg |
| Magnesium stearate | 1.0 kg |
| Highly dispersed silicia | 0.5 kg |
| Lactose | 100.5 kg |
| | 168.0 kg |

Production

The highly dispersed silica magnesium stearate and 4 kg of microcrystalline cellulose were passed through a hand sieve having a mesh width of 0.5 mm and homogeneously mixed in a kneader for about 10 minutes to produce Mixture I.

Lactose, the product of Example 1 and the remaining amount of microcrystalline cellulose were sieved through a vibrating screen having a mesh width of 0.8 mm and after addition of Mixture I homogeneously mixed in a mixer to form a "Composition Ready For Molding". Relative humidity of the "Composition Ready For Molding": 30%±5%.

The "Composition Ready For Molding" was molded to curved tablets on a rotary pelleting press or an eccentric press Weight: 140 mg
Diameter: 7 mn
Surface: curved
Radius of curvature: 5 mm
Thickness: 3.9±0.1 mm
Hardness: minimum 5 kg
Decomposition time in water at 20° C.: maximum 4 minutes.

What is claimed is:

1. 7-azabenzimidazole of the formula

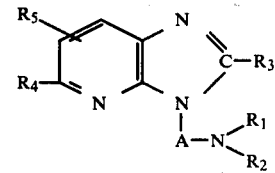

where $R_1$ is hydrogen or $C_1$–$C_6$ alkyl and $R_2$ is $C_1$–$C_6$ alkyl or $C_2$–$C_6$ alkanoyl, $R_3$ is hydroxy, a mono $C_1$–$C_6$-alkylamino group, or a di-$C_1$–$C_6$-alkylamino group, $R_4$ is halogen, amino, mono $C_1$–$C_6$ alkylamino, di-$C_1$–$C_6$ alkylamino, mercapto, $C_1$–$C_6$-alkylmercapto, hydroxy or $C_1$–$C_6$-alkoxy, $R_5$ is hydrogen or halogen and A is a $C_2$–$C_6$ alkylene group or a salt of such compound.

2. A compound according to claim 1, wherein $R_1$ and $R_2$ are the same and are $C_1$–$C_6$ alkyl, $R_3$ is hydroxy, or mono or di $C_1$–$C_6$-alkylamino $R_4$ is halogen, amino, mono $C_1$–$C_6$ alkylamino, di-$C_1$–$C_6$ alkylamino, mercapto, $C_1$–$C_6$-alkylmercapto, hydroxy or $C_1$–$C_6$-alkoxy and $R_5$ is hydrogen or an addition salt thereof with a pharmaceutically acceptable acid.

3. A compound according to claim 2, where $R_4$ is halogen.

4. A compound according to claim 3, where $R_4$ is chlorine.

5. A compound according to claim 4, where $R_3$ is hydroxy.

6. A compound according to claim 2, where $R_3$ is hydroxy.

7. A compound according to claim 1, wherein $R_3$ is hydroxy.

8. A compound according to claim 1, wherein A is a $C_2$–$C_3$ alkylene group, $R_1$ is hydrogen, methyl or ethyl, $R_2$ is methyl or ethyl, $R_3$ is hydroxy, $R_4$ is chlorine, methylamino, $C_1$–$C_3$-alkoxy, dimethylamino or methyl mercapto and $R_5$ is hydrogen or chlorine.

9. A compound according to claim 1 wherein $R_2$ is $C_1$–$C_6$ alkyl.

10. A compound according to claim 9 wherein $R_3$ is hydroxy.

11. A compound according to claim 1 where $R_4$ is $C_1$–$C_6$-alkoxy.

12. A compound according to claim 11 where $R_3$ is hydroxy.

13. A compound according to claim 12 where $R_1$ is hydrogen or $C_1$–$C_6$ alkyl and $R_2$ is $C_1$–$C_6$ alkyl.

14. A compound according to claim 13 where $R_1$ is $C_1$–$C_6$ alkyl.

15. A compound according to claim 14 where $R_5$ is hydrogen.

16. A compound according to claim 15 which is 1-(2-diethylaminoethyl)-2-hydroxy-6 methoxy-7-aza-benzimidazole.

17. A medicament containing as an active ingredient in an amount sufficient to provide protective action against ulcers a compound of claim 1 together with a pharmaceutical excipient or diluent.

18. A method of combatting ulcers in a mammal an amount of a compound of claim 1 effective to protect against ulcers.

19. A method according to claim 18, wherein the compound is administered orally.

20. A method according to claim 19, wherein the compound is administered orally at least 0.1 mg/kg body weight of the mammal.

21. A method according to claim 18, wherein the compound is administered intravenously.

22. A method according to claim 21, wherein the compound is administered intravenously at least 0.1 mg/kg body weight of the mammal.

23. A method of reducing gastritis, thinning secrolytic mucous, or retarding stomach secretions in a mammal comprising administering to the mammal are amount of a compound of claim 1 effective for such purpose.

24. A method of combatting ulcers in a mammal comprising administering to the mammal an amount of a compound having the formula

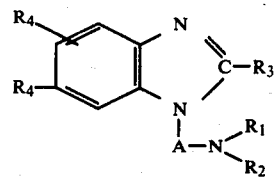

where $R_1$ is hydrogen or $C_1$–$C_6$-alkyl and $R_2$ is $C_1$–$C_6$-alkyl or $C_2$–$C_6$ alkanoyl, $R_3$ is hydroxy, an amino group, a mono $C_1$–$C_6$-alkylamino group, a di-$C_1$–$C_6$-alkylamino group or a $C_2$–$C_6$-alkanoylamino group, $R_4$ is halogen, amino, mono $C_1$–$C_6$ alkylamino, di-$C_1$–$C_6$ alkylamino, mercapto, $C_1$–$C_6$-alkylmercapto, hydroxy or $C_1$–$C_6$-alkoxy, $R_5$ is hydrogen or halogen and A is a $C_2$–$C_6$ alkylene group or a salt of such compound effective to protect against ulcers.

25. A method of reducing gastritis, thinning secrolytic mucous, or retarding stomach secretions in a mammal comprising administering to the mammal an amount of a compound having the formula

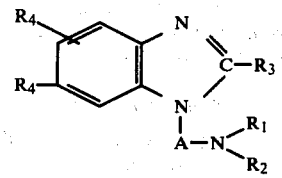

where $R_1$ is hydrogen or $C_1$–$C_6$-alkyl and $R_2$ is $C_1$–$C_6$-alkyl or $C_2$–$C_6$ alkanoyl, $R_3$ is hydroxy, an amino group, a mono $C_1$–$C_6$-Alkylamino group, a di-$C_1$–$C_6$-alkylamino group or a $C_2$–$C_6$-alkanoylamino group, $R_4$ is halogen, amino, mono $C_1$–$C_6$ alkylamino, di $C_1$–$C_6$ alkylamino, mercapto, $C_1$–$C_6$-alkylmercapto, hydroxy or $C_1$–$C_6$-alkoxy, $R_5$ is hydrogen or halogen and A is a $C_2$–$C_6$ alkylene group or a salt of such compound effective to protect against ulcers.

* * * * *